US00PP08833P

United States Patent [19]

Fruehwirth

[11] Patent Number: Plant 8,833

[45] Date of Patent: Jul. 12, 1994

[54] POINSETTIA PLANT 490 MARBLE

[75] Inventor: Franz Fruehwirth, Encinitas, Calif.

[73] Assignee: Paul Ecke Ranch, Inc., Encinitas, Calif.

[21] Appl. No.: 96,660

[22] Filed: Jul. 23, 1993

[51] Int. Cl.[5] ..... A01H 5/00

[52] U.S. Cl. ..... Plt./86.1

[58] Field of Search ..... Plt. 86.1

*Primary Examiner*—James R. Feyrer

*Attorney, Agent, or Firm*—Arnold, White & Durkee

[57] ABSTRACT

Poinsettia '490 Marble' is a new cultivar, distinguished by pink and creamy white bicolored bracts and intense dark green foliage with self-branching characteristics. '490 Marble' is a color sport of the dark red bracted '490' (U.S. Plant Pat. No. 7,825) with the same early flowering response and cultural requirements. The new plant produces a very desirable branched flowering pot plant. It is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an induced pink and white bicolored bracted sport of '490' (U.S. Plant Pat. No. 7,825) in my greenhouse in Encinitas, Calif. It was induced through irradiation of a group of 100 vegetative plants of '490' with 4000 rads of gamma radiation randomly applied to the whole plant. A single plant from the irradiated group exhibited pink and creamy white bicolored bracts and intense dark green foliage. The mutant was characterized by its early flowering, self-branching, dark green foliage, and pink and white bicolored flower bracts; traits which distinguished it from other poinsettia cultivars on the market and seem to make it a desirable plant for commercial greenhouse production. No other similar plants were observed from the irradiation nor were any other changes in the plant observed which would appear to have commercial merit. '490 Marble' differed from its parent '490' in having pink and creamy white bicolored bracts as compared to the dark red bracts of '490' but otherwise had characteristics similar to the parent. After selection, '490 Marble' was vegetatively reproduced from stem cuttings for test purposes in Encinitas, Calif. By subjecting clones of this plant to successive generations of vegetative propagation, it was demonstrated that the distinctive characteristics of '490 Marble' held true from generation to generation.

DESCRIPTION OF THE PHOTOGRAPHS

Poinsettia '490 Marble' is illustrated in the accompanying color photographs. The upper photo is a side view of a typical branched plant in full flower. The lower photo is a top view of the same plant showing flower and bract formation.

DESCRIPTION OF THE PLANT

The following is a detailed description of this new poinsettia as observed in Encinitas, Calif., U.S.A., during December 1992. Observations were recorded from flowering plants, grown as one branched plant per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of '490' (U.S. Plant Pat. No. 7,825), induced through irradiation of vegetative plants with 4000 rads of radiation.

Classification:

*Botanic.*—*Euphorbia pulcherrima* Willd.

*Common name.*—Poinsettia.

*Cultivar name.*—'490 Marble'.

Form: Shrub.

Height: Short.

Growth habit: As a branched plant, upright and short. The application of a chemical growth retardant may not be needed to restrict height for commercial pot plant reduction. I observed a branched plant in a pot with an overall height of 38 cm. and an overall width of 40 cm. The bract diameter of individual flowers was 24 cm.

Branching: Axillary branches will develop and terminate in a flower without pinching. However, it is usually desirable to pinch '490 Marble' and remove all terminal dominance. Then, all axillary branches will develop uniformly and at a faster rate.

Growth rate: Rooting of stem cuttings occurs in 12–18 days under intermittent mist.

Flowering: The plant will flower in about eight weeks under continuous long night conditions and night temperatures of about 16–18 degrees C. Like its parent ('490'), '490 Marble' will be in full bloom in mid-November in the northern hemisphere under natural daylength conditions. '490 Marble' flowers earlier than most known poinsettias because flower induction seems to occur in mid-September, about 10 days earlier than normal.

Foliage: At flowering, plants were observed with about 11 uniformly dark green leaves on each stem, one leaf per node. The leaves were of medium size, leaf blades typically 14–15 cm. long and 9–11 cm. wide with leaf petioles 6–7 cm. long.

*Leaf shape.*—Typical leaves are generally ovate with obtuse bases and acuminate tips. Leaf margins are mostly entire or slightly lobed with 1 or 2 indentations on each side of the leaf blade.

*Color.*—Upper side — Dark green, much darker than RHS 147A.

Bracts: Generally there were 12–15 pink and white bicolored bracts of various sizes subtending the cyathia. The primary bracts have blades typically 13–14 cm. long and 7–8 cm. wide with petioles about 2 cm. long.

*Shape.*—Primary bracts are ovate with acute bases and acuminate tips and weakly lobed with 1 small indentation on either side of the bract. Secondary bracts are elliptic and have entire margins.

*Color.*—Upper side — Bicolored: Pink and creamy white on each bract. An irregular area of pink, between RHS 47D and 48C, is located at the center of the bracts, usually on either side of the mid-vein. The creamy white color, near RHS 4D, is peripheral to the pink. Under side — Bicolored: Pink and creamy white. The pattern of each color mostly mirror the upper surface. The pink is between RHS 47D and 48C. The peripheral creamy white is near RHS 4D.

Flowers:

*Cyathia.*—Generally, 10–12 cyathia (flowers) are present on each stem when the plant is in full bloom. Each cyathium was about 6 mm long and 6 mm wide, green in color, and fringed with creamy white at the distal end. A yellow nectar cup protrudes from the side of each cyathium. The flower pedicel is also green and about 4 mm in length. The stamens protruding from the cyathia are reddish. The anthers are bifurcate with copious yellow pollen.

*Nectar exudate.*—Abundant.

*Seeds.*—Self-incompatible.

*Fertility.*—Not observed.

Post production: '490 Marble' is resistant to epinasty after being confined to shipping containers and recovers rapidly if the plant does become epinastic. The foliage and bract retention are excellent even under low light intensities in the consumer's home.

What is claimed is:

1. A new and distinct Poinsettia cultivar, substantially as herein shown and described, distinguished by its intense dark green foliage, pink and creamy white bicolored bracts, self branching, early flowering and good leaf and bract retention in the consumer environment.

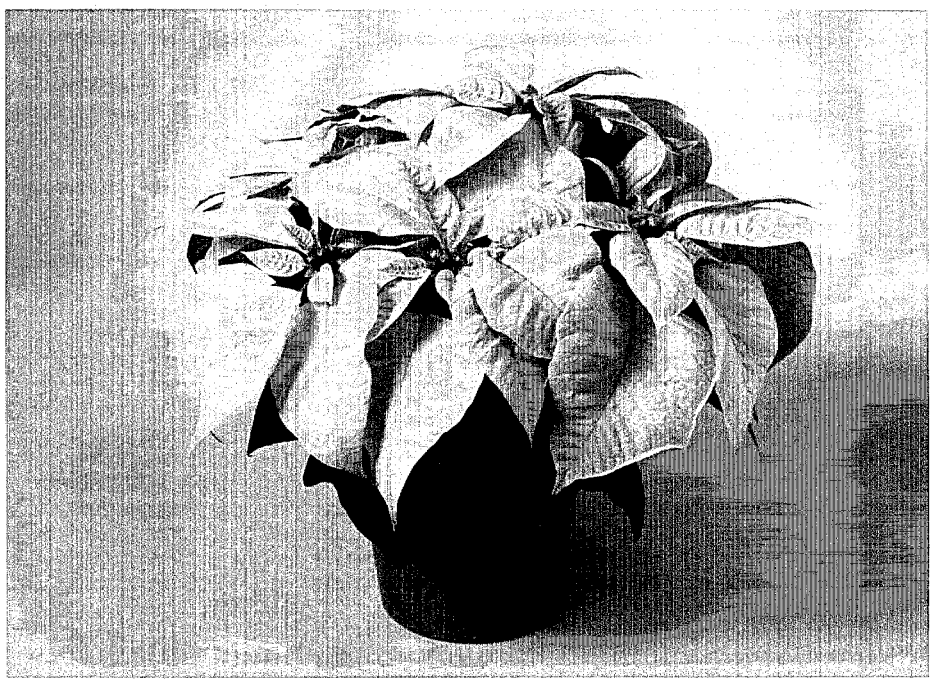
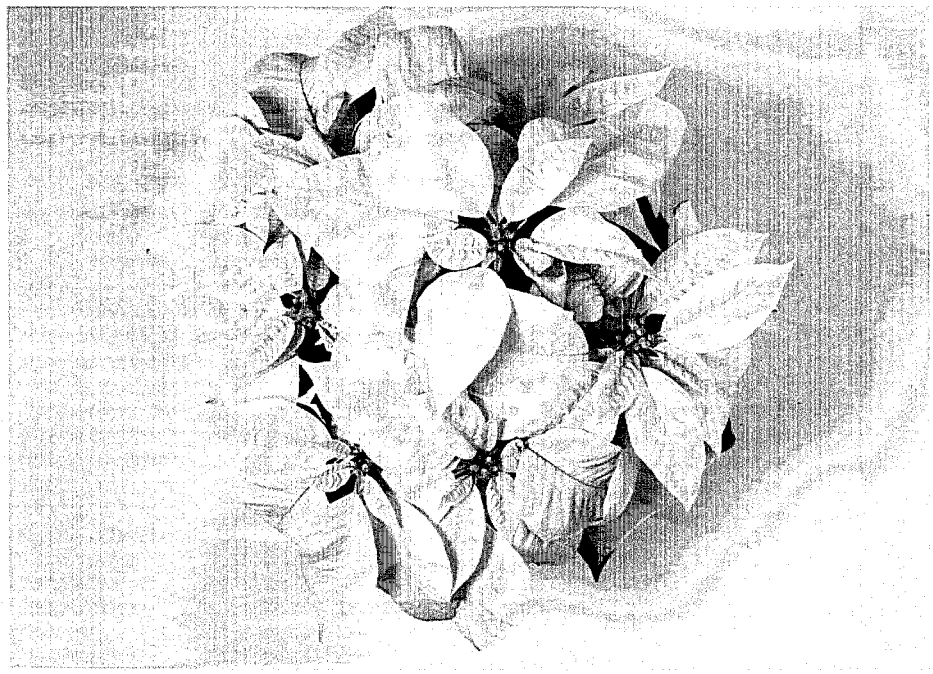

* * * * *